United States Patent [19]
Joly et al.

[11] Patent Number: 5,744,681
[45] Date of Patent: Apr. 28, 1998

[54] PARAFFIN ALKYLATION PROCESS

[75] Inventors: Jean-François Joly, Lyon; Alain Forestiere, Vernaison; Jean-Luc Duplan, Irigny; Eric Benazzi, Montesson, all of France

[73] Assignee: Institut Francais du Petrole, Rueil Malmaison, France

[21] Appl. No.: 620,456

[22] Filed: Mar. 22, 1996

[30] Foreign Application Priority Data

Mar. 24, 1995 [FR] France ................... 95 03590
Mar. 24, 1995 [FR] France ................... 95 03592

[51] Int. Cl.$^6$ ............................ C07C 2/56; C07C 2/58; C07C 2/60
[52] U.S. Cl. .................. 585/709; 585/714; 585/716; 585/719; 585/720; 585/721
[58] Field of Search ............... 585/709, 714, 585/719, 716, 720, 721

[56] References Cited

U.S. PATENT DOCUMENTS

| | | | |
|---|---|---|---|
| 2,314,333 | 3/1943 | Francis | 585/730 |
| 2,348,467 | 5/1944 | Goldsby et al. | 585/730 |
| 2,420,369 | 5/1947 | Goldsby et al. | 585/730 |
| 2,450,174 | 9/1948 | Weinrich et al. | 585/741 |
| 5,157,196 | 10/1992 | Crossland et al. | 585/720 |
| 5,221,777 | 6/1993 | Huss, Jr. et al. | 585/730 |
| 5,336,833 | 8/1994 | Joly et al. | 585/731 |
| 5,420,093 | 5/1995 | Joly et al. | 585/730 |
| 5,489,728 | 2/1996 | Benazzi et al. | 585/730 |
| 5,489,729 | 2/1996 | Bennazzi et al. | 585/730 |

*Primary Examiner*—Margaret Medley
*Attorney, Agent, or Firm*—Millen, White, Zelano & Branigan, P.C.

[57] ABSTRACT

A process for the alkylation of at least one isoparaffin by at least one olefin in the presence of at least one solid acidic catalyst, characterized in that the major portion of the olefin is initially brought into contact with the catalyst in a complexing zone to form an olefin-catalyst complex in the presence of the isoparaffin, and in that the suspension of the complex in the isoparaffin is then sent to at least one alkylation reaction zone.

24 Claims, 2 Drawing Sheets

PARAFFIN ALKYLATION PROCESS

The present invention concerns a novel process for the alkylation of at least one isoparaffin, preferably isobutane, by at least one olefin generally containing 3 to 6 carbon atoms per molecule.

BACKGROUND OF THE INVENTION

Spark ignition internal combustion engines, in particular high compression ratio engines, require fuels with high octane numbers, i.e., mainly constituted by highly branched paraffinic hydrocarbons. The alkylation of isoparaffins (isobutane and/or isopentane) by olefins containing 3 to 6 carbon atoms per molecule can produce such products. The reaction requires the use of highly acidic catalysts, mainly to reduce side reactions such as hydride extraction from the olefin and polymerization which produce less highly branched hydrocarbons with low octane numbers and unsaturated hydrocarbons, cracking reactions and dismutation reactions.

Existing processes for the production of hydrocarbons by alkylation of isobutane by olefins use either sulphuric acid or hydrofluoric acid as the catalyst. In those processes, the acidic catalyst constitutes a liquid phase which is brought into contact with the liquid isobutane-olefin mixture to form an emulsion. Those processes are expensive and encounter major problems regarding safety of personnel and the environment. In order to overcome these problems, catalytic systems other than sulphuric acid and hydrofluoric acid in the liquid phase have been sought.

A number of patents claim the use of heterogeneous catalysts (alumina combined with $BF_3$, for example) in Grignard type stirred reactors (International patent WO 92/03395, U.S. Pat. No. 4,918,255, U.S. Pat. No. 3,655,813). That use of the catalyst has a number of drawbacks, namely the destruction of the catalyst by attrition over time. Further, obtaining short residence times for hydrocarbons in the reactor is technically difficult to achieve.

The use of fixed bed(s) of heterogeneous alkylation catalysts has been described in European patent application EP-A-0 433 954, and in U.S. Pat. No. 3,852,371 and U.S. Pat. No. 3,976,713; in that case, obtaining very high dilution of the olefin close to the catalyst grains is difficult and further, large pressure drops are associated with the use of catalysts with low granulometry.

U.S. Pat. No. 5,157,196 claims the use of alkylation catalysts in a circulating bed, characterized by introducing an olefin into the reactor, and a mixture of catalyst and paraffin.

SUMMARY OF THE INVENTION

The present invention concerns a process for the catalytic alkylation, generally termed aliphatic alkylation, of at least one isoparaffin, for example isobutane and/or isopentane, by at least one olefin, generally $C_3$–$C_6$, in the presence of at least one solid acidic catalyst, to produce at least one product, for example belonging to the group constituted by dimethylbutanes, trimethylpentanes, trimethylhexanes and trimethylheptanes.

The alkylation reaction is characterized by high exothermicity (about 20 kcal/mol, i.e., 83.6 kJ/mol of butene transformed for the alkylation of isobutane by $C_3$–$C_6$ olefins). The process of the present invention enables alkylation to be carried out under the best conditions, in particular obtaining good homogeneity of temperature and of reactant concentration.

The present invention concerns a process for the alkylation of at least one isoparaffin by at least one olefin in the presence of at least one solid acidic catalyst, characterized in that at least part, preferably the major portion and more preferably substantially all, of the olefin is initially brought into contact with the catalyst in a complexing zone to form an olefin-catalyst complex in the presence of the isoparaffin, and in that the suspension of the complex in the isoparaffin is then sent to an alkylation zone.

The "complex" formed between the olefin and the catalyst results from a reaction which involves at least one proton $H^+$, initially present in the catalyst or originating from one of the compounds present. Without subscribing to a particular theory, the interaction between the olefin and the proton $H^+$ leads to the formation of a carbocation $R^+$. The counter-ion $X^-$ associated with the carbocation is a species belonging to the catalyst. As an example, when the catalyst comprises the acid phase $H_2SO_4$, $X^-$ is $HSO_4^-$; when the catalyst includes the acid phase HF, $X^-$ is $F^-$; when the catalyst includes the acid phase $CF_3SO_3H$, $X^-$ is $CF_3SO_3^-$; when the catalyst includes the acid phase SbF5,HF, $X^-$ is $SbF6^-$. When sulphuric acid is included in the catalyst and when but-1-ene is the olefin, the complex is the compound nC4+SO4H$^-$.

The operating conditions in the isoparaffin alkylation process of the invention, in particular the temperature and pressure, are selected so that the mixture constituted by the isoparaffin, olefin(s) and reaction products are liquid. Further, it is important that the solid catalyst is immersed in the liquid to ensure good liquid-solid contact everywhere. This avoids the occurrence of dry zones in the reaction zone, which zones could reduce thermal stability, since dry zones can reach high temperatures because the reaction may occur entirely in the gaseous phase in these regions. A number of techniques have been proposed which use a continuous liquid phase, the catalyst being used in the form of a suspension, ebullating bed, fixed bed or expanded bed, or as a circulating or fluidized bed.

The process of the present invention can be applied to any solid catalyst which is a Bronsted acid (protonic), comprising an amorphous support, for the alkylation of at least one isoparaffin, more particularly isobutane and/or isopentane, by at least one olefin generally containing 3 to 6 carbon atoms per molecule.

The catalyst present in zone R is selected from solid catalysts which are known to the skilled person. It includes an amorphous support, preferably silica and sulphuric acid, the silica being completely impregnated with sulphuric acid. The silica is generally selected so that its total pore volume is greater than 0.5 cm$^3$/g. The catalyst obtained after impregnation is for example, such that the sulphuric acid content is greater than 45% by weight, preferably greater than 75%.

The silica can contain impurities such as oxides, alkalis, alkaline-earths, aluminum compounds or any other impurity which is known to the skilled person, the total quantity of impurities not exceeding 2% by weight with respect to the silica.

The catalyst is preferably selected from the following catalysts:

a catalyst comprising at least sulphuric acid impregnated into an organic or inorganic porous support, such as the catalysts described in European patent applications EP-A-0 539 277, EP-A-0 542 612, EP-A-0 542 620, EP-A-0 559 511, EP-A-0 643 992, EP-A-0 643 993, EP-A-0 645 183 and EP-A-0 645 184;

a catalyst comprising a mixture containing at least one halide of a compound selected from the group formed by aluminum and boron, and at least one quaternary ammonium halide and/or amine halohydrate, such as the catalyst described in European patent application EP-A-0 553 009.

The concentration of the acid, preferably sulphuric acid, is advantageously in the range 90% to 100% by weight, preferably in the range 97% to 100% by weight and more preferably in the range 98% to 100% by weight.

In the preferred case when the acid is sulphuric acid, before impregnation into the amorphous support, additives aimed at improving catalytic performance can be added. Examples of such additives are the trifluoromethanesulphonic acid $CF_3SO_3H$ and acid $HB(SO_4H)_4$, and preferably boric acid $BO_3H_3$ or boric anhydride.

Preferred catalysts for use in the present invention are of the sulphuric acid on silica type, preferably doped with a boron compound.

The average diameter (or equivalent) of the catalyst particles, generally mainly constituted by substantially spherical grains, is generally in the range 0.1 to 200 µm, preferably in the range 10 to 80 µm, and more preferably in the range 10 to 60 µm.

In a preferred implementation of the invention, the process is characterized in that the major portion of a liquid feed comprising the olefin and isoparaffin is introduced to the extremity of at least one complexing zone (C), in that the olefin is brought into contact with the catalyst in said complexing zone to form in part, preferably the major portion, more preferably substantially completely, a complex with the catalyst, in the presence of the isoparaffin, and in that the major portion of the suspension of the complex (complexed catalyst) in the isoparaffin is sent to at least one alkylation zone (R).

The process of the invention may be carried out as follows:

the catalyst, preferably suspended in a mixture of hydrocarbons which is generally rich in isoparaffin, and a portion, preferably the major portion, of the feed containing at least a mixture of isoparaffin and olefin are introduced to one extremity of a complexing zone (C);

the olefin, isoparaffin and catalyst are circulated in zone (C) so that the catalyst and the major portion of the olefin form a complex;

the isoparaffin and a major portion, preferably substantially all, of said complex are extracted from the other extremity of zone (C);

the major portion of the complex suspended in the isoparaffin, extracted from zone (C), is introduced into an alkylation zone (R);

at least a portion of the catalyst is extracted from zone (R);

the reaction effluent, preferably containing practically no catalyst, is extracted from zone (R);

said reaction effluent is separated in a separation zone into at least one alkylate and a mixture of hydrocarbons which is rich in isoparaffin;

the major portion of the catalyst extracted from zone (R) is sent to the extremity of the complexing zone into which the feed to be treated is introduced.

In a first variation, at least a portion of the isoparaffin-rich hydrocarbon mixture from the separation zone is recycled to zone (R).

In a second variation, which may or may not be independent of the first variation, at least a portion of the isoparaffin-rich hydrocarbon mixture from the separation zone is recycled to mix it with the catalyst between its extraction from zone (R) and introduction into zone (C).

In a third variation, which may or may not be independent of the two preceding variations, at least a portion of the isoparaffin-rich hydrocarbon mixture from the separation zone is recycled to zone (C).

The preceding variations may be combined together.

The process of the invention is such that the feed is introduced at several points in zone (C), one of which is the extremity.

The process of the invention is such that the major portion of the complex in suspension in the isoparaffin is introduced into zone (R) at several points, at least one point being the inlet to said zone.

In one implementation of the process of the present invention, the process uses a circulating bed. In this case, the process is preferably such that a feed comprising a stoichiometric mixture of at least one isoparaffin, preferably at least one isoparaffin selected from the group formed by isobutane and isopentane, more preferably isobutane, is treated with at least one olefin, preferably containing 3 to 6 carbon atoms per molecule, in the presence of a solid acidic catalyst, said process comprising:

a) introducing the following compounds into a complexing zone (C) and bringing them into contact:
  (i) the feed, preferably introduced at least in part at least one extremity of zone (C), said extremity preferably being the upper portion of zone (C);
  (ii) a suspension of catalyst in a mixture of isoparaffin-rich hydrocarbons recycled from the step described at d);

during which contact the major portion, preferably substantially all, of the olefin in the feed forms a complex with a portion of the catalyst;

b) introducing the major portion of the catalyst suspension leaving zone (C) into a reaction zone (R) (preferably into the upper portion of zone (R));

c) extracting a liquid effluent which is substantially free of catalyst from zone (R) then introducing the major portion of this liquid effluent into a separation zone (S) to separate an isoparaffin-rich fraction, a normal paraffin-rich fraction and an alkylate-rich fraction;

d) extracting a suspension of a portion of catalyst from zone (R) (preferably from the lower portion of zone (R)), and transferring it to zone (C).

e) obtaining an alkylate as a product, extracted from zone (S) (generally from the lower portion of zone (S)); and optionally f) obtaining normal-butane as a purge from zone (S).

The operating conditions of this circulating bed implementation are described below.

The temperature in the complexing zone (C) is generally in the range −20° C. to +6° C., preferably in the range −16° C. to 0° C., and the pressure is generally such that all the hydrocarbon is liquid in that zone.

The heat produced in zone (C) is preferably eliminated by at least one heat exchanger located at the outlet to zone (C) and before the inlet to zone (R).

The temperature in zone (R) is generally in the range −12° C. to +10° C., preferably in the range −10° C. to +5° C., and the pressure is generally such that all the hydrocarbon is liquid in that zone.

The heat produced in zone (R) is preferably removed by at least one heat exchanger located at the outlet to zone (R) and before the inlet to zone (C).

The residence time for the catalyst in zone (C) is generally in the range 1 second to 5 minutes, preferably in the range 1 to 60 seconds, more preferably in the range 1 to 10 seconds. The residence time is preferably selected such that, at the temperature used in zone (C), the major portion and preferably substantially all of the olefin disappears from the liquid hydrocarbon phase.

The residence time for the catalyst in zone (R) is generally in the range 30 seconds to 1 hour, preferably in the range 1 to 30 minutes and more preferably in the range 1 to 10 minutes. The residence time is preferably selected such that at the temperature used in zone (R), conversion of the complex formed by the olefin and catalyst is substantially complete.

The feed has preferably been dried over a molecular sieve and selectively hydrogenated before introducing it into zone (C) to eliminate highly unsaturated compounds which could inhibit the catalytic phase.

In general, the feed is introduced at the inlet, or at the inlet and at other points in zone (C), so that the hourly space velocity, expressed as the weight of olefin(s) introduced per unit weight of catalyst present in zones (C) and (R) and per hour is generally in the range 0.01 to 10 h$^{-1}$, preferably in the range 0.02 to 2 h$^{-1}$, and more preferably in the range 0.025 to 1 h$^{-1}$.

The concentration by volume of catalyst in zones (C) and (R), expressed as the volume of catalyst per volume of liquid hydrocarbon phase, is generally in the range 1:100 to 1:1, preferably in the range 1:100 to 1:50, and more preferably in the range 1:50 to 1:4.

In order to limit secondary reactions degrading $C_5$–$C_{12}$ isoparaffins present in the liquid effluents passing through zones (C) and (R), separation is preferably carried out so that the ratio of mass flow rates of isoparaffin (for example isobutane) at the head of zone (S) and alkylate from the bottom of zone (S) is in the range 5:1 to 100:1, preferably in the range 10:1 to 30:1.

In the present implementation of the process of the invention, where the process is a circulating bed process, a plurality of complexing zones and a plurality of reaction zones can be used, each complexing zone being followed by a reaction zone, a catalyst suspension circulating, either continuously or periodically, through all the complexing zones and all the reaction zones, the feed being divided such that it is distributed at least in part to at least one extremity of each complexing zone such that in each complexing zone the major portion, preferably substantially all, of the olefin forms a complex with the catalyst circulating therein, in which process the major portion, preferably substantially all, of the catalyst extracted from the last reaction zone is returned to the first complexing zone and in which the major portion of the reaction effluent from the last reaction zone is sent to the separation zone where, in particular, an alkylate is recovered and an isoparaffin fraction is recovered, the major portion of which is returned to the first complexing zone mixed with the major portion of the catalyst extracted from the last reaction zone. Catalyst may be purged from each reaction zone.

In the present implementation of the process of the invention, deactivated catalyst is extracted from the reaction zone or zones (R) either continuously or discontinuously, and fresh catalyst or regenerated catalyst is introduced into those reaction zone or zones (R). The quantity of catalyst extracted is equal to the quantity of catalyst introduced.

In a further implementation of the process of the present invention, the process uses an expanded bed, a fixed bed, a stirred bed or an ebullating bed. In this case, the process is preferably such that a feed comprising a stoichiometric mixture of at least one isoparaffin, preferably selected from the group formed by isobutane and isopentane, more preferably isobutane, is treated with at least one olefin, preferably containing 3 to 6 carbon atoms per molecule, in the presence of a solid acidic catalyst, said process comprising:

a) introducing and bringing into contact a suspension of catalyst described below in c), and the feed, during which contact the major portion, preferably substantially all, of the olefin in the feed forms a complex with a portion of the catalyst, in a complexing zone (C);

b) introducing the catalyst suspension leaving zone (C) defined at c) into a reaction zone (R);

c) periodically or continuously extracting a portion of the catalyst suspension from zone (R);

d) extracting from zone (R) a liquid effluent which is substantially free of catalyst and sending at least the major portion of this effluent to a separation zone (S) from which is recovered at least one isoparaffin-rich fraction, at least one n-paraffin-rich fraction and at least one alkylate-rich fraction;

e) recycling to the reaction zone at least a portion, preferably the major portion, and more preferably substantially all, of the isoparaffin-rich fraction recovered from separation zone (S) in step d);

f) obtaining an alkylate as a product, extracted from zone (S) (generally from the lower portion of zone (S)); and optionally g) obtaining normal-butane as a purge from zone (S).

In step c), the catalyst is extracted from zone (R) in suspension in a mixture which is generally rich in isoparaffin.

The major portion of the catalyst thus generally remains in the reaction zone (R) until the end of the alkylation reaction.

In the present preferred implementation of the process of the invention, the suspension of the catalyst in the isoparaffin of step b) can be introduced at a plurality of points in reaction zone (R). These different injection points are distributed along zone (R), and at least one of these injection points is the inlet to said zone (R).

Preferably, complexing zone (C) is formed in at least one conduit for the suspension of catalyst, extracted from zone (R) and transferred to zone (R); it is thus possible to introduce the feed at a plurality of points in said conduit where the major portion, preferably substantially all, of the olefin is complexed. These different injection points are distributed along the conduit and one of these injection points is the inlet to said conduit.

In the present preferred implementation of the process of the invention, the compound described in e) can be introduced at a plurality of points in zone (R). These different injection points are, for example, distributed along the reaction zone, and one of these injection points is the inlet to said zone. The distribution is effected so as to be most advantageous for the course of the reaction, depending on the operating conditions and the compounds present in zone (R).

In the present implementation of the process of the invention, the reaction zone comprises at least one fixed bed, ebullating bed, expanded bed or stirred bed reactor. In this implementation, the catalyst is stirred by the mixture described at step e). One of the advantages of this preferred implementation is that the speed of the liquid in zone (R) regulates the height of the catalytic bed, i.e., its expansion for example. Other advantages of this implementation are the facility with which catalyst can be added to or extracted from zone (R), possible elimination from the liquid by entraining the catalyst grains which have lost material by attrition, and obtaining good agitation near the catalyst grains while limiting intergrain shock.

The operating conditions for the present implementation of the process of the invention are described below.

The temperature in zone (R) is generally in the range −30° C. to +5° C., preferably in the range −15° C. to +5° C., and the pressure is generally such that all the hydrocarbon injected into zone (R), at whatever level of the injection, is liquid on injection into the zone. Heat is preferably eliminated using at least one heat exchanger.

The temperature in zone (C) is generally in the range −20° C. to 0° C., preferably in the range −15° C. to 0° C., and the pressure is generally such that all the hydrocarbon injected into zone (C), at whatever level of injection, is liquid on injection into the zone.

The feed has preferably been dried over a molecular sieve and selectively hydrogenated before introducing it into complexing zone (C) to eliminate highly unsaturated compounds which could inhibit the catalytic phase.

The ratio of the mass flow rate of catalyst to that of the olefin coming into contact therewith to complex with the catalyst is generally in the range 10 to 100.

The reactants are introduced so that the hourly space velocity, expressed as the weight of olefin(s) introduced into zone (R) (in the complexed form) per unit weight of catalyst present in zone (R) and per hour, is generally in the range 0.01 to 10 $h^{-1}$, preferably in the range 0.02 to 2 $h^{-1}$, and more preferably in the range 0.025 to 1 $h^{-1}$.

The ratio of the mass flow rate of catalyst and of the olefin in the feed is generally in the range 10 to 100, preferably in the range 20 to 500, and more preferably in the range 100 to 500.

The residence time of the catalyst in zone (C) is generally in the range 1 to 5 seconds. The residence time of the catalyst in reaction zone (R) is generally in the range 3 minutes to 2 hours.

In the present implementation of the process of the invention, where the process uses a fixed bed, ebullating bed, expanded bed or stirred bed, a plurality of reaction zones and a plurality of complexing zones can be used. When a plurality of reaction zones is used in series, each reaction zone is preceded by a complexing zone. In this case, it is advantageous to introduce the isoparaffin from the separation zone (S) only at the inlet to the first reaction zone, the olefin then being introduced at the inlet to each of the olefin complexing zones, to form the desired complex with a portion of recycled catalyst from each reaction zone. Thus the isoparaffin from the separation zone is recycled in totality to the first reaction zone, the feed being divided into as many fractions as there are reaction zones, the olefin of each fraction being complexed by a suspension of catalyst from at least one reaction zone towards which the catalyst-olefin complex is directed. If the reaction zones are in parallel, each reaction zone is preceded by a complexing zone and each reaction zone receives a portion of the isoparaffin-rich recycling effluent and appropriate quantities of olefin and isoparaffin (fresh and recycled from the head of separation zone (S)) via distribution means which are known to the skilled person. Here again, in the olefin inlet conduits in each complexing zone, contact takes place with a portion of recycled catalyst from at least one of the reaction zones. Thus in this process, the isoparaffin from a separation zone is divided into as many fractions as there are reaction zones, each fraction being recycled to each reaction zone, the feed also being divided into as many fractions as there are reaction zones, the olefin in each fraction being complexed by a suspension of catalyst from at least the reaction zone towards which the catalyst-olefin complex will be directed. When using a plurality of reaction zones (disposed in series or in parallel), the olefin admitted into each reaction zone is not compulsorily complexed with catalyst extracted from the corresponding reaction zone but can be complexed with catalyst from one or other of the other reaction zones. In the case of reactors in parallel, one separation zone per reaction zone can be used.

BRIEF DESCRIPTION OF THE DRAWINGS

The accompanying figures illustrate the invention.

The feed to be converted, constituted by a liquid mixture in line 1 and comprising at least one isoparaffin (preferably at least one isoparaffin selected from the group formed by isobutane and isopentane) and at least one olefin generally containing 3 to 6 carbon atoms per molecule, is mixed with a suspension of catalyst in a mixture which is rich in isoparaffin from line 6, then introduced to the top of a complexing zone C.

The catalyst suspension leaving the bottom of complexing zone C passes through exchanger E2 and is then introduced via line 2 to the top of reaction zone R. A liquid effluent containing excess isoparaffin and alkylation reaction products (alkylate) is extracted from reaction zone R via line 3. The mass flow rate of this effluent is equal to the mass flow rate of the feed (line 1).

The effluent is then introduced into an isoparaffin/normal-paraffin/alkylate separation zone (zone S). The alkylate separated in zone S is extracted from the unit as a product via line 7. Normal-paraffin is extracted as a side stream from via line 8, as a purge. The isoparaffin-rich liquid fraction extracted overhead from zone S is recycled to the complexing zone inlet via lines 5, 11 and 6, after mixing with the suspension of catalyst leaving reaction zone R via line 4 and passing through an exchanger E1.

Used catalyst can be extracted from the unit via line 9 (purge); new catalyst to maintain the productivity of the unit is introduced into reaction zone R via line (10).

Figure 1:
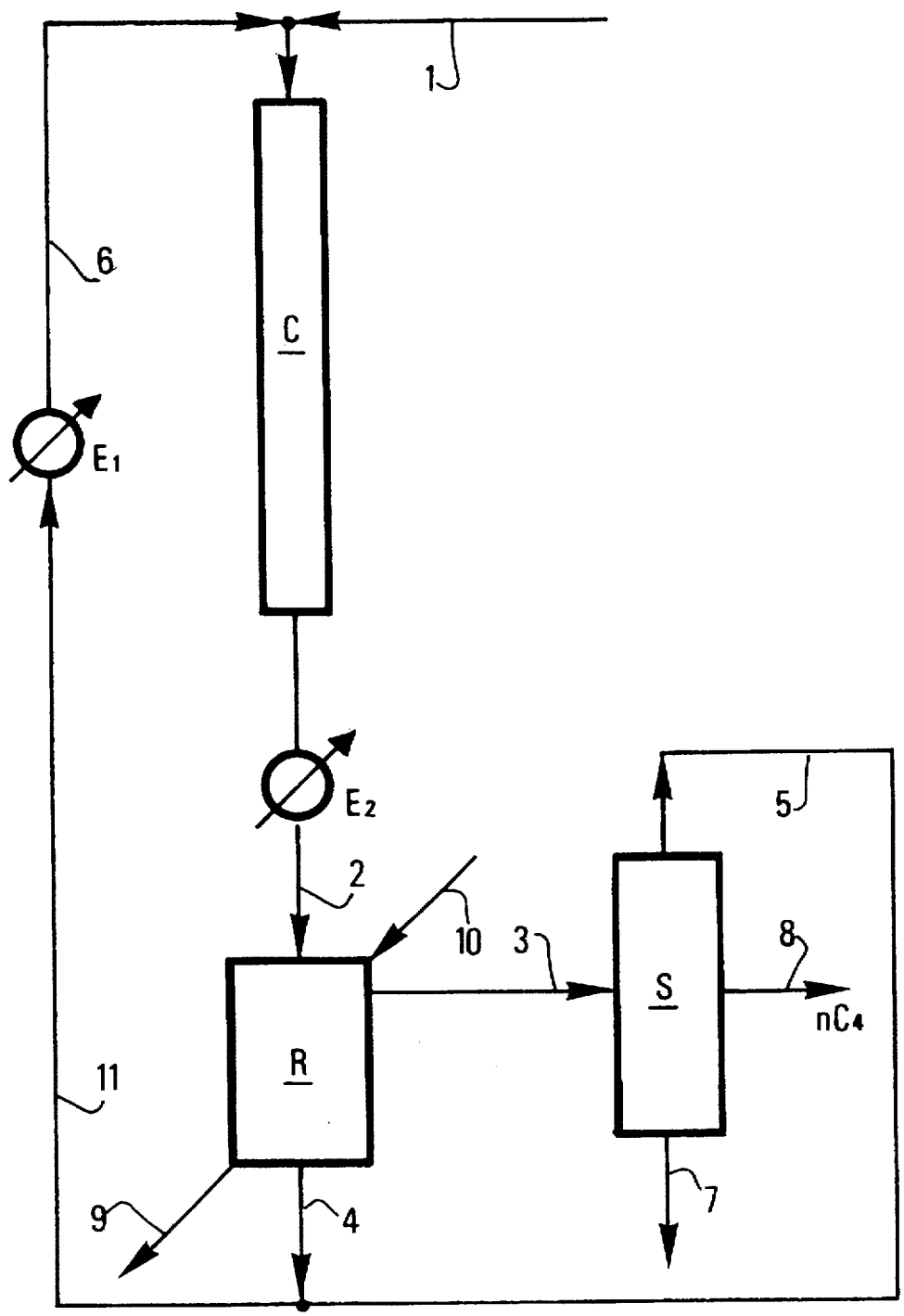
FIG. 1 illustrates the implementation of the invention using a circulating bed process.
Figure 2:
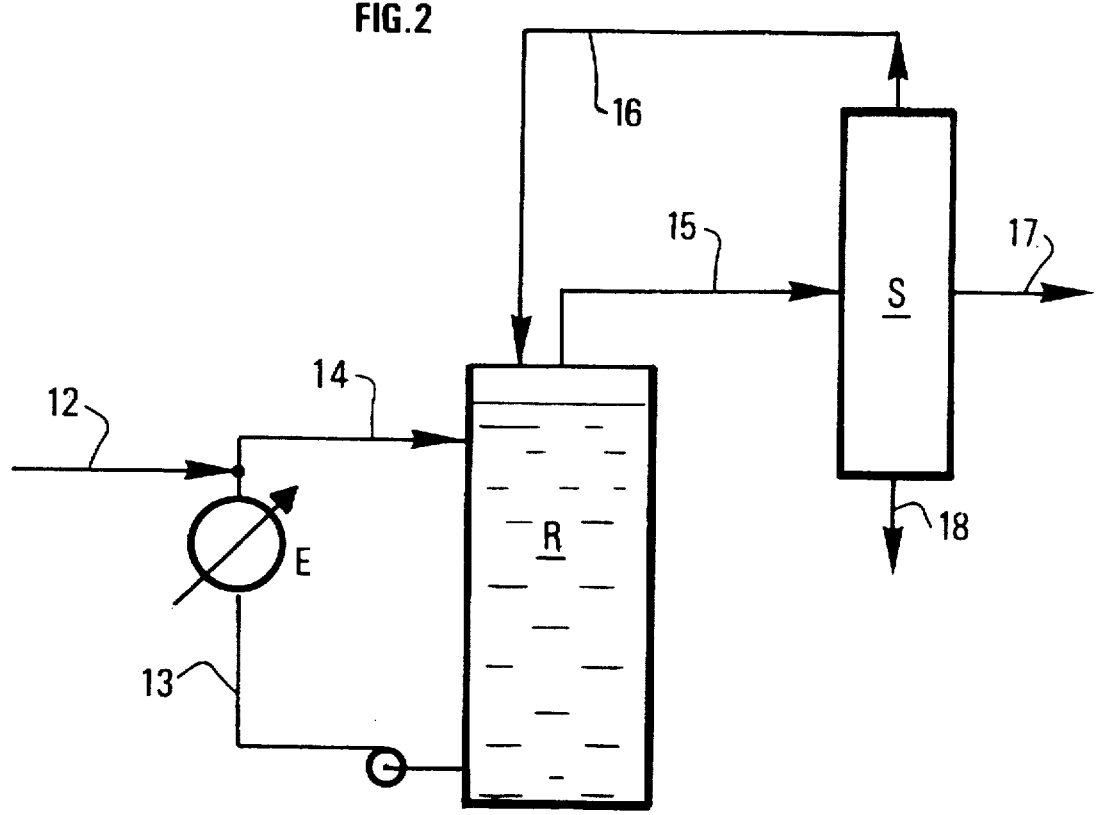

FIG. 2 illustrates the implementation of the process of the invention using a fixed bed, ebullating bed, stirred bed or expanded bed.

The liquid mixture, comprising isoparaffin and at least one olefin containing 3 to 6 carbon atoms per molecule, is introduced via line (12) into a conduit (13) in which circulates a mixture of a suspension of catalyst in a liquid effluent composed of a mixture of isoparaffin, normal-paraffin and alkylate from reactor R. The mixture constituted by lines 12 and 13 is introduced into reactor R via line 14.

A heat exchanger E in line 13 cools the suspension of catalyst extracted from the reactor before bringing it into contact with the effluent from line 12. This exchanger eliminates the heat liberated by the complexing reaction between the olefin and catalyst and thus maintains the liquid in the reactor at the desired temperature.

A liquid effluent containing no suspended catalyst leaves zone R via line 15 and is sent to isoparaffin/normal-paraffin/alkylate separation zone S. The alkylate separated in zone S is extracted from the unit as a product via line 18. Normal-paraffin is extracted as a side stream via line 17, as a purge. The isoparaffin-rich liquid fraction extracted overhead from zone S is generally at least partially recycled to the inlet to reaction zone R via line 16.

EXAMPLES

The following examples illustrate the invention without in any way limiting its scope.

EXAMPLE 1

Circulating Bed Process

Composition of Catalyst

The catalyst was composed of 17% by weight of a silica with an average particle diameter of 70 μm and an acid phase containing 60% by weight of anhydrous sulphuric acid and 40% by weight of the compound $HB(HSO_4)_4$.

Alkylate Production Unit

It was intended to produce 187.5 g/h of alkylate from a feed with the following composition by weight:
propane:0.84
n-butane:12.00
isobutane:44.34
but-1-ene:17.16
but-2-ene:24.98
isobutene:0.68
184 g of catalyst was used.

Four complexing zones were alternated with four reaction zones in series and operating adiabatically. The totality of isobutane recycled from the fractionating column following the fourth reaction zone, i.e., 3800 g/h, was introduced after mixing with the catalyst suspension leaving the fourth reactor to the inlet to the first complexing zone. The overall flow rate at the inlet to this first complexing zone was 5300 g/h, of which 1500 g/h was catalyst. The temperature of the suspension was −15° C. The feed to be converted was introduced to the inlet of each of the four complexing zones at a flow rate of 53.7 g/h (of which 23 g/h was olefins). After passage through a heat exchanger at the outlet to the first complexing zone, the temperature of the catalyst suspension had risen to −8° C. At the outlet to the first reactor the catalyst suspension was cooled again to bring the temperature to −15° C. The unit was operated such that the inlet temperatures to the complexing zones were identical and equal to −15° C. and such that the temperatures at the inlets to the reaction zones were identical and equal to −8° C. The totality of the alkylate produced in the four reactors was extracted from the fourth reactor and sent to the fractionating column.

The volumes of the four complexing zone were identical and equal to 15 ml, the volumes of the reaction zones were equal to 184 ml. The total volume of the four reaction zones was thus 736 ml.

The alkylate produced had the following composition by weight:
iC5:3.30
iC6:3.39
iC7:2.88
iC8:77.79
iC9:1.60
iC10+:11.04

The calculated motor and research octane numbers were respectively 93.5 and 96.4.

EXAMPLE 2

Expanded Bed Process

Composition of Catalyst

The catalyst was composed of 17% by weight of a silica with an average particle diameter of 90 μm and an acid phase containing 60% by weight of anhydrous sulphuric acid and 40% by weight of the compound $HB(HSO_4)_4$.

Alkylate Production Unit

It was intended to produce 187.5 g/h of alkylate from a feed with the following composition by weight:
propane:0.84
n-butane:12.00
isobutane:44.34
but-1-ene:17.16
but-2-ene:24.98
isobutene:0.68

Four reactors were used in series, all operating as expanded beds. The totality of the isobutane recycled from the outlet of zone S was injected into the inlet to the first reactor. Each of four equal portions of the feed to be treated was introduced into the inlet of one reactor.

Each reactor had a volume of 350 ml and contained 300 g of catalyst. The surface velocity of the liquid (feed+ recycled isobutane+products) was close to 0.5 cm/s, sufficient to expand the catalyst with an expansion ratio of about 30%.

The liquid effluent, containing excess isobutane and reaction products, was sent to a deisobutanizer. The excess isobutane, condensed overhead of the deisobutanizer, was recycled to the inlet to the first reactor. A debutanizer was used to eliminate the n-butane present in the alkylate at the base of the deisobutanizer.

The flow rate of the recycled isobutane was 286 g/h.

Each reactor was equipped with an external conduit which connected the top and bottom portions of the expanded bed via the exterior of the reactor. A suspension of the catalyst in the liquid hydrocarbon phase from the reactor circulated at a rate of 470 g/h in this conduit. For each reactor, the feed to be treated (a quarter of the total feed), described above, was introduced via a connection in said conduit to adsorb the olefin on the catalyst. The flow rate of the feed introduced into the conduit in each reactor was 89.5 ml/h. The ratio of catalyst flow rate/olefin flow rate where the feed contacted the catalyst in the conduit was 15 by weight. The conduit was equipped with a heat exchanger which produced a temperature of −10° C. at the outlet to the olefin complexing conduit.

The residence time of the catalyst in the conduit was 5 seconds.

The total pressure in the conduit and the reactor was $5 \times 10^5$ Pa.

The alkylate produced had the following composition by weight after elimination of butane:
iC5:1.24
iC6:1.89
iC7:1.43
TMPs:84
DMHs:8
iC9:0.25
iC10+:3.19

The motor and research octane numbers were respectively 95.7 and 99.2.

We claim:

1. A process for the alkylation of at least one isoparaffin by at least one olefin in the presence of at least one solid acidic catalyst, which comprises bringing a major portion of the olefin into contact with the catalyst in a complexing zone to form an olefin-catalyst complex, in the presence of the isoparaffin, before the complex is sent to at least one alkylation zone.

2. A process according to claim 1, further comprising introducing a major portion of a liquid feed comprising the olefin and isoparaffin at the extremity of at least one complexing zone (C), such that the olefin is brought into contact with the catalyst in said complexing zone to form a suspension of the complex with the catalyst in the isoparaffin, and sending the suspension to at least one alkylation zone (R).

3. A process according to claim 1, in which a major portion of the olefin is complexed by the catalyst.

4. A process according to claim 1, in which
the catalyst and a portion of a feed containing a mixture of isoparaffin and olefin is introduced to one extremity of a complexing zone (C);
the olefin, isoparaffin and catalyst are circulated in zone (C) so that the catalyst and a major portion of the olefin form a complex suspended in the isoparaffin;
a major portion of said complex and the isoparaffin are extracted from the other extremity of zone (C);
a major portion of the complex suspended in the isoparaffin is introduced into an alkylation reaction zone (R);
at least a portion of the catalyst is extracted from zone (R);
the reaction effluent is extracted from zone (R);
said reaction effluent is separated in a separation zone into at least one alkylate and a mixture of hydrocarbons which is rich in isoparaffin;
a major portion of the catalyst extracted from zone (R) is sent to the extremity of the complexing zone into which the feed is introduced.

5. A process according to claim 4 in which at least a portion of the mixture of hydrocarbons rich in isoparaffin from the separation zone is recycled to zone (R).

6. A process according to claim 4, in which at least a portion of the mixture of hydrocarbons rich in isoparaffin from the separation zone is recycled to mix it with the catalyst extracted from zone (R) before it is sent to the extremity of the complexing zone.

7. A process according to claim 4, in which at least a portion of the mixture of hydrocarbons rich in isoparaffin from the separation zone is recycled to zone (C).

8. A process according to claim 2, in which the feed is introduced at more than one point in zone (C), one of which is the extremity.

9. A process according to claim 2, in which the major portion of the complex in suspension in the isoparaffin is introduced into zone (R) at more than one point, at least one point being the inlet to said zone.

10. A process according to claim 2, using a circulating bed.

11. A process according to claim 10, in which a feed comprising a stoichiometric mixture of at least one isoparaffin is treated with at least one olefin in the presence of a solid acidic catalyst, said process comprising:
a) introducing the following compounds into a complexing zone (C) and bringing them into contact:
(i) the feed;
(ii) a suspension of catalyst in a mixture of isoparaffin-rich hydrocarbons recycled from the step described at d); during which contact the major portion of the olefin in the feed forms a complex with a portion of the catalyst;
b) introducing the major portion of the catalyst suspension leaving zone (C) into a reaction zone (R);
c) extracting a liquid effluent which is substantially free of catalyst from zone (R) then introducing the major portion of this liquid effluent into a separation zone (S) to separate an isoparaffin-rich fraction, a normal paraffin-rich fraction and an alkylate-rich fraction;
d) extracting a suspension of a portion of catalyst from zone (R) and transferring it to zone (C),
e) obtaining an alkylate as a product, extracted from zone (S); and optionally
f) obtaining normal-butane as a purge from zone (S).

12. A process according to claim 10, in which the temperature in the complexing zone (C) is in the range −20° C. to +6° C., the residence time of the feed is in the range 1 second to 5 minutes, and the pressure is such that all the hydrocarbon is liquid in said zone, and in which the temperature in the alkylation reaction zone (R) is in the range −12° C. to +10° C., the residence time of the feed is in the range 30 seconds to 1 hour, and the pressure is such that all the hydrocarbon is liquid in said zone.

13. A process according to claim 10, in which the feed is introduced into zone (C) such that the hourly space velocity, expressed as the weight of olefin(s) introduced per unit weight of catalyst present in zones (C) and (R) per hour, is in the range 0.01 to 10 h$^{-1}$, the concentration by volume of catalyst in said zones, expressed as the volume of catalyst per volume of liquid hydrocarbon, being in the range 1:100 to 1:1.

14. A process according to claim 10, in which a plurality of complexing zones and a plurality of reaction zones are used, each complexing zone being followed by a reaction zone, a suspension of catalyst circulating continuously or periodically through all the complexing zones and all the reaction zones, the feed being divided so as to be distributed at least in part to at least one extremity of each complexing zone so that in each complexing zone the major portion of the olefin forms a complex with the catalyst circulating therein, in which process the major portion of the catalyst extracted from the last reaction zone is returned to the first complexing zone and in which the major portion of the reaction effluent from the last reaction zone is sent to the separation zone from which an alkylate and an isoparaffin fraction are recovered, the major portion of the isoparaffin fraction being sent to the first complexing zone mixed with the major portion of the catalyst extracted from the last reaction zone.

15. A process according to claim 2 using an expanded bed, fixed bed, stirred bed or ebullating bed.

16. A process according to claim 15, wherein the feed comprises a stoichiometric mixture of at least one isoparaffin and at least one olefin is treated in the presence of a solid acidic catalyst, said process comprising:
a) introducing and bringing into contact a suspension of catalyst described below in c), and the feed, during which contact the major portion of the olefin in the feed forms a complex with a portion of the catalyst, in a complexing zone (C);
b) introducing the catalyst suspension leaving zone (C) defined at c) into a reaction zone (R);
c) periodically or continuously extracting a portion of the catalyst suspension from zone (R);
d) extracting from zone (R) a liquid effluent which is substantially free of catalyst and sending the major portion of this effluent to a separation zone (S) from which is recovered at least one isoparaffin-rich fraction, at least one n-paraffin-rich fraction and at least one alkylate-rich fraction;
e) recycling to the reaction zone at least a portion of the isoparaffin-rich fraction recovered from separation zone (S) in step d);

f) obtaining an alkylate as a product, extracted from zone (S); and optionally g) obtaining normal-butane as a purge from zone (S).

17. A process according to claim 15, in which the temperature in complexing zone (C) is in the range −20° C. to 0° C., and the pressure is such that all the hydrocarbon is liquid in said zone, and in which the temperature in the alkylation reaction zone (R) is in the range −30° C. to +5° C., and the pressure is such that all the hydrocarbon is liquid in said zone.

18. A process according to claim 15, in which the hourly space velocity, expressed as the weight of olefin introduced into the reaction zone per unit weight of catalyst present in said zone per hour, is in the range 0.01 to 10 h$^{-1}$.

19. A process according to claim 15, in which the ratio of the mass flow rate of the catalyst and the olefin coming into contact therewith to complex the olefin is in the range 10 to 100.

20. A process according to claim 15, in which the ratio of the mass flow rate of catalyst to the flow rate of olefin present in the feed to be treated is in the range 10 to 1000.

21. A process according to claim 15, in which the residence time of the catalyst in zone (C) is in the range 1 to 5 seconds, the residence time of the catalyst in zone (R) being in the range 3 minutes to 2 hours.

22. A process according to claim 15, in which the suspension of catalyst is extracted periodically or continuously from zone (R).

23. A process according to claim 1, in which the isoparaffin is selected from the group consisting of isobutane and isopentane and in which the olefin contains 3 to 6 carbon atoms per molecule.

24. The process of claim 1, wherein the olefin-catalyst complex is a complex of a carbocation of the olefin with an anion of the acid of the catalyst.

* * * * *